US00PP34403P2

(12) United States Plant Patent
Bradford et al.

(10) Patent No.: US PP34,403 P2
(45) Date of Patent: Jul. 5, 2022

(54) NECTARINE TREE NAMED 'PEARLICIOUS XI'

(50) Latin Name: *Prunus persica*
Varietal Denomination: 'Pearlicious XI'

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,923

(22) Filed: Dec. 17, 2021

(51) Int. Cl.
*A01H 5/08* (2018.01)
*A01H 6/74* (2018.01)

(52) U.S. Cl.
USPC ..... Plt./188
CPC ..... *A01H 6/7454* (2018.05)

(58) Field of Classification Search
USPC ..... Plt./188
CPC ..... A01H 6/7454; A01H 5/08
See application file for complete search history.

(56) References Cited

U.S. PATENT DOCUMENTS

PP18,778 P2 4/2008 Bradford

*Primary Examiner* — Keith O. Robinson

(57) ABSTRACT

The present invention relates to a new and distinct variety of nectarine tree, *Prunus persica*, broadly characterized by a small size, moderately vigorous, hardy, self-fertile, productive and regular bearing tree. The variety blooms during the mid to late season and requires about 550 chilling hours. The fruit matures under the ecological conditions described in late July, with first picking on Jul. 26, 2021. The fruit is uniform, large in size, a tasty balance of high sugar with light acid in flavor, globose to slightly oblate in shape, clingstone in type, firm in texture, white in flesh color, full red with minimal freckling in skin color, and has a bitter tasting kernel.

1 Drawing Sheet

Botanical classification: *Prunus persica.*
Variety denomination: 'PEARLICIOUS XI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Pearlicious XI'.

In 2013 we made a first generation hybridization using '26P994' (unpatented) nectarine as the selected seed parent and 'Majestic Pearl' (U.S. Plant Pat. No. 18,778) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2018 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, '26P994' (unpatented) nectarine, by being self-fertile and by producing nectarines that are clingstone in type, large in size, sub-acidic in flavor, and full red in skin color, but is quite distinguished from it by producing nectarines that are white instead of yellow in flesh color, that are substantially sweeter in flavor, and that ripen about 20 days later.

The present variety is most similar to its pollen parent, 'Majestic Pearl' (U.S. Plant Pat. No. 18,778) nectarine by being self-fertile, by having reniform leaf glands, by having a bitter kernel, and by producing nectarines that are white in flesh color, clingstone in type, large in size, and firm in texture, but is distinguished therefrom by having a smaller tree, by blooming about 4 days later, and by producing nectarines that are a fuller red in skin color, that are slightly oblate instead of slightly oblong in shape, that are sweeter with a little more detectable acid in flavor, and that ripen nine days later.

SUMMARY OF VARIETY

In summary, the present nectarine variety is characterized by a small size, moderately vigorous, hardy, self-fertile, productive and regular bearing tree. The variety blooms during the mid to late season and requires about 575 chilling hours. The fruit matures under the ecological conditions described in late July, with first picking on Jul. 26, 2021. The fruit is uniform, large in size, a tasty balance of high sugar with slight acid in flavor, globose to slightly oblate in shape, clingstone in type, firm in texture, white in flesh color, full red with minimal freckling in skin color, and has a bitter tasting kernel.

DRAWING

The accompanying photograph consists of four whole fruits positioned to display the characteristics of the skin color and form, one divided fruit to reveal the flesh and stone, typical leaves, a tip shoot growth, and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 30, 2021, on the original tree during its eighth growing season. The blossom and flower descriptions were made the previous blooming season. All major color code designations are by reference to the Inter-Society Color Council, National Bureau of Standards. Common color names are also used occasionally.

PARENTAGE

Seed parent: '26P994' (unpatented) nectarine.
Pollen parent: 'Majestic Pearl' (U.S. Plant Pat. No. 18,778) nectarine.

TREE

Size: Small, reaching and maintaining a height of 9' [2.74 m.] and a spread of 8' [2.44 m.] after eight growing seasons utilizing typical dormant pruning.
Vigor: Medium vigor, responding about average to irrigation and fertilization. The variety grows about 2' [0.61 m.] of surplus top-growth during the spring and summer. The plant should be grown on a standard commercial rootstock for production purposes.
Growth: Spreading and moderately dense.
Form: Pruned to a perpendicular or parallel V shape.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning usually necessary.
Fertility: Self-fertile.
Bearing: Regular bearer, with no crop failures observed.
Chilling requirement: About 575 hours.
Leaf bud burst: Medium to late, during the end of flowering.
Trunk:
- *Size*.—Slender, reaching a maximum diameter of 4¼" [108 mm.] after the eighth growing season.
- *Texture*.—Somewhat rough.
- *Bark color*.—A Light grayish brown [60. l.gy.Br] and Light brownish gray [63. l.brGy] variegation with Dark grayish brown [62. d.gy.Br] crevices present.
- *Lenticels*.—Approximate Number Per Square Inch: 8. Color: Strong yellowish brown [74. s.yBr]. Average Size: ⅜" [9.5 mm.] in length. The width is typically one fourth as much as the length. Shape: Elongated.

Branches:
- *Size*.—Slender, diameter of main scaffold is 2⅛" [54.0 mm.] measured 12" above the crotch, diameter of limb is ⅞" [22.2 mm.] measured 12" above the first fork.
- *Texture*.—Smooth to medium on first and second year wood, increasing in roughness with age.
- *Color*.—1st Year Wood Topside: Grayish red [19. gy.R]. 1st Year Wood Underside: Brilliant yellow green [116. brill.YG]. Older Wood: A Light brownish gray [63. l.brGy] and Brownish gray [64. brGy] variegation with Strong brown [55. s.Br] cervices present.
- *Lenticels*.—Number Per Square Inch: About 25 on second year wood. Color: Strong yellowish brown [74. s.yBr]. Average Size: Small, 1/16" [1.6 mm.] in length. The width is typically one fourth as much as the length. Shape: Elongated.

Leaves:
- *Size*.—Large. Average Length: 5½" [139.7 mm.]. Average Width: 1⅞" [47.6 mm.].
- *Arrangement*.—Alternate.
- *Thickness*.—Medium.
- *Form*.—Elliptical.
- *Apex*.—Acuminate.
- *Base*.—Acute, with an average base angle of 75 degrees.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Petiole*.—Average Length: ⅜" [9.5 mm.]. Average Thickness: 1/16" [1.6 mm.]. Color: Brilliant yellow green [116. brill.YG].
- *Stipules*.—Number: 2 per leaf, up to 6 per growing tip. Average Length: ¼" [6.4 mm.]. Color: Pale yellow green [121. p.YG] becoming Moderate brown [58. m.Br] with age.
- *Glands*.—Number: 2 to 4 per leaf. Position: Alternate, first pair is located at the intersection of petiole and base of blade. Form: Reniform. Size: Medium to large, about 1/32" [0.8 mm.] in diameter. Color: Brilliant yellow green [116. brill.YG] becoming Dark yellowish brown [78. d.yBr] with age.
- *Leaf buds*.—Pointed.

Flower buds:
- *Hardiness*.—Hardy, with respect to central California blooming season.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Light purplish pink [249. l.pPk].

Flowers: Perfect, complete, perigynous, usually a single pistil, about thirty stamens, five sepal and petal locations alternately positioned.
- *Type*.—Showy, large.
- *Average flower diameter*.—1 15/16" [49.2 mm.].

*Average flower depth.*—½" [12.7 mm.] when fully open.
*Number of petals.*—Five, extra petal fragments very numerous, double blossoms occasionally observed.
*Petal arrangement.*—Overlapping.
*Petal shape.*—Circular.
*Petal margin.*—Entire, very wavy with a few notches.
*Average petal diameter.*—13/16" [20.6 mm.].
*Average petal length.*—13/16" [20.6 mm.].
*Petal apex.*—Rounded.
*Petal base.*—Rounded.
*Petal color.*—Pale purplish pink [252. p.pPk] toward the apex and Light purplish pink [249. l.pPk] toward the base on both sides.
*Anthocyanin coloration intensity.*—Weak.
*Anther color.*—Moderate red [15. m.R] surrounding a Light yellow [86. l.Y] center at bloom onset.
*Pollen.*—Anthers produce an abundance of Brilliant yellow [83. brill.Y] pollen.
*Stigma color.*—Light greenish yellow [101. l.gY].
*Stigma position.*—Typically located about even with the nearby anthers.
*Stamen position.*—Typically located about 1/16" [1.6 mm.] below the petals.
*Average pistil length.*—¾" [19.1 mm.].
*Average stamen length.*—9/16" [14.3 mm.].
*Ovary.*—Non-pubescent.
*Sepal color.*—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length.*—5/16" [7.9 mm.].
*Sepal width.*—5/16" [7.9 mm.].
*Sepal apex.*—Rounded to elliptical to match the sepal length and width.
*Sepal margin.*—Fairly smooth.
*Sepal outer surface.*—Pubescent.
*Fragrance.*—Moderate in degree with a slight hint of rose.
*Blooming period.*—Medium to late, blooms about four days after 'Majestic Pearl' (U.S. Plant Pat. No. 18,778) nectarine.
*Onset of bloom.*—One percent on Feb. 23, 2021.
*Date of full bloom.*—Mar. 5, 2021.
*Duration of bloom.*—One to two weeks, dependent on ambient temperature.
*Bloom density.*—Medium to heavy.
*Number per cluster.*—1 to 3 with single flowers most common.

FRUIT

Maturity when described: Firm ripe, Jul. 30, 2021
Date of first picking: Jul. 26, 2021.
Date of last picking: Aug. 10, 2021.
Size: Uniform, large.
*Average diameter axially.*—3 1/16" [77.8 mm.].
*Average diameter across suture plane.*—3⅜" [85.7 mm.].
*Average diameter across cheek plane.*—3 5/16" [84.1 mm.].
*Typical weight.*—10.3 ounces [291 grams].
Form: Uniform, globose to slightly oblate, mostly symmetrical.
*Longitudinal section form.*—Round to slightly oblate.
*Axial view.*—Round.
Suture: Extends from the stem through the shoulder, completely smooths out along the side, and becomes a groove across the apex ending about ½" [12.7 mm.] beyond the pistil point.
*Near the base.*—A very shallow groove.
*Along the side.*—Mostly flat, with a few shallow troughs and a few slightly bulging outward.
*Near the apex.*—A shallow groove.
Ventral surface: Rounded.
Lips: Fairly equal across the apex.
Cavity: Flaring, circular, suture showing on one side, small Pale yellow [89. p.Y] stem markings present on most.
*Depth.*—⅝" [15.9 mm.].
*Breadth.*—1 7/16" [36.5 mm.].
Base: Truncate.
Apex: Rounded, quite cordate if viewed parallel to the suture.
Pistil point: Askew, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to the flesh.
*Astringency.*—Very slightly astringent.
*Tendency to crack.*—None observed.
*Color.*—Very deep red [14. v.deep R] over a Deep Red [13. deep R] background with very minor Light yellow [86. l.Y] freckling toward the apex. The primary color is about seventy-five percent of the total skin area, and the background color is about twenty-five percent.
Flesh:
*Color.*—Yellowish white [92. yWhite] with Deep red [13. deep R] streaking and flecking toward the stone.
*Surface of pit cavity.*—Covered with Very deep red [14. v.deep R] broken fibers when twisted away from the stone.
*Amygdalin.*—Slight.
*Juice.*—Abundant, rich.
*Texture.*—Firm, crisp.
*Fibers.*—Few, fine.
*Ripens.*—Fairly even, earliest at the shoulders.
*Flavor.*—A tasty balance of high sugar with slight acid, typically 21 brix.
*Aroma.*—Wanting.
*Eating quality.*—Excellent.

STONE

Type: Clingstone.
Size: Medium.
Form: Oval.
Hilum: Narrow, oblong.
Base: Rounded.
Apex: Rounded with a sharp tip protruding.
Sides: Equal.
Tip: Sharp, 1/32" [0.8 mm.] in length.
Surface: Irregularly furrowed toward the apex, pitted toward the base.
Ridges: Rounded.

External color: Deep reddish brown [41. deep rBr] when first removed.
Pit wall color when cracked: Strong brown [55. s.Br].
Cavity surface color: Strong yellowish brown [74. s.yBr].
Average pit wall thickness: 3/16" [4.8 mm.].
Average length: 1 3/8" [34.9 mm.].
Average width: 1 1/16" [27.0 mm.].
Average breadth: 7/8" [22.2 mm.].
Tendency to split: None observed.
Kernel:
*Form*.—Oval.
*Skin color*.—Light yellow [86. l.Y].
*Pellicle color*.—Dark brown [59. d.Br].
*Vein color*.—No veins observed.
*Taste*.—Bitter.
*Viable*.—Yes.
*Average length*.—7/8" [22.2 mm.].
*Average width*.—5/8" [15.9 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree named 'Pearlicious XI', substantially as illustrated and described, that is most similar to 'Majestic Pearl' (U.S. Plant Pat. No. 18,778) nectarine by being self-fertile, by having reniform leaf glands, by having a bitter kernel, and by producing nectarines that are white in flesh color, clingstone in type, large in size, and firm in texture, but is distinguished therefrom by having a smaller tree, by blooming about 4 days later, and by producing nectarines that are a fuller red in skin color, that are slightly oblate instead of slightly oblong in shape, that are sweeter with a little more detectable acid in flavor, and that ripen nine days later.

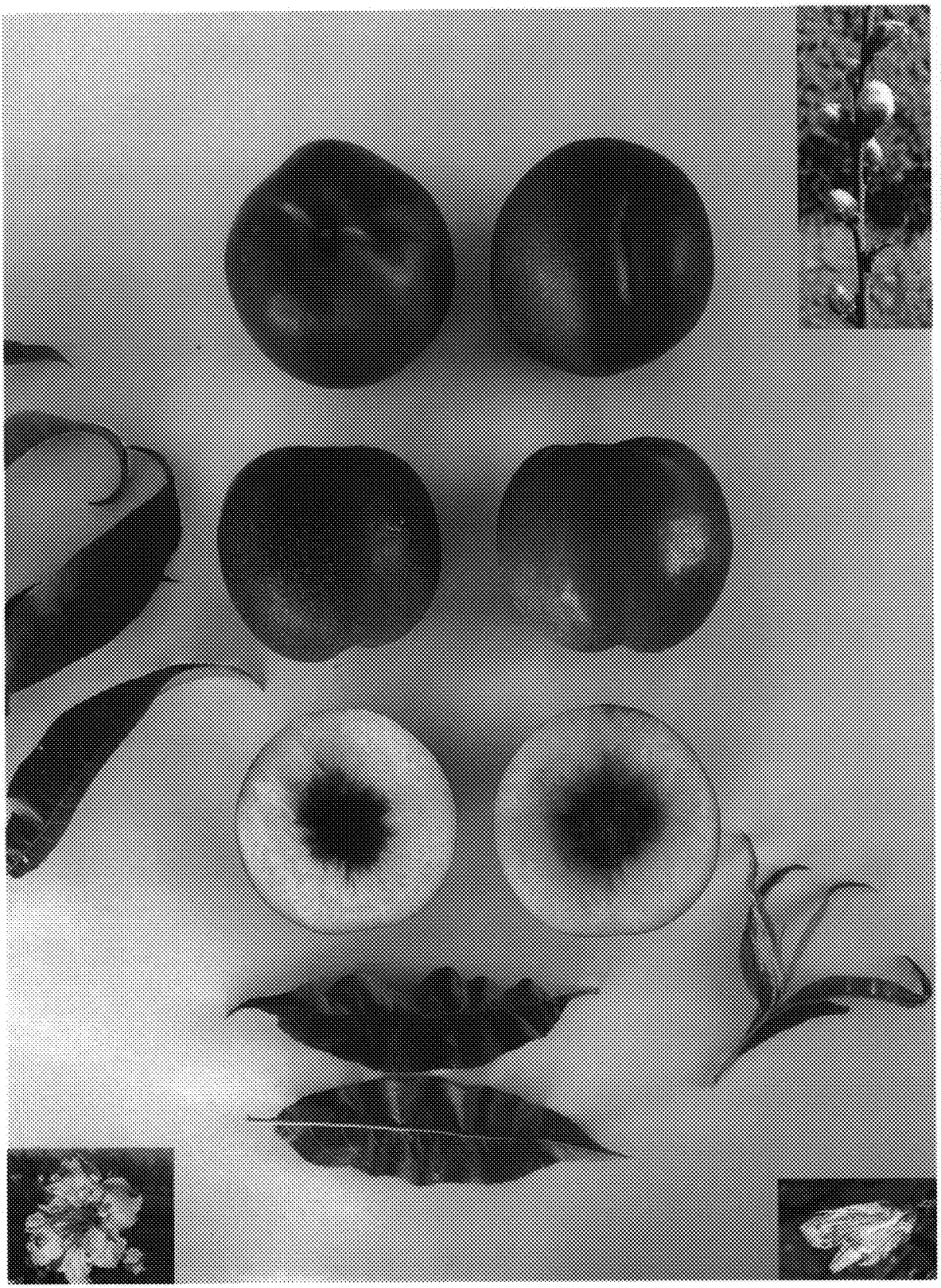

* * * * *